US007872114B2

(12) United States Patent
Pizza et al.

(10) Patent No.: US 7,872,114 B2
(45) Date of Patent: Jan. 18, 2011

(54) IMMUNOGENIC DETOXIFIED MUTANTS OF CHOLERA TOXIN

(75) Inventors: Mariagrazia Pizza, Siena (IT); Maria Rita Fontana, Siena (IT); Valentina Giannelli, Monteroni d'Arbia (IT); Rino Rappuoli, Monteriggioni (IT)

(73) Assignee: Novartis Vaccines and Diagnostics SRL, Siena (IT)

( * ) Notice: Subject to any disclaimer, the term of this patent is extended or adjusted under 35 U.S.C. 154(b) by 163 days.

(21) Appl. No.: 10/986,582

(22) Filed: Nov. 12, 2004

(65) Prior Publication Data

US 2005/0136076 A1 Jun. 23, 2005

Related U.S. Application Data

(63) Continuation of application No. 10/611,398, filed on Jun. 30, 2003, now Pat. No. 7,632,513, which is a continuation of application No. 09/819,917, filed on Mar. 28, 2001, now abandoned, which is a continuation of application No. 08/981,208, filed as application No. PCT/IB96/00703 on Jul. 1, 1996, now abandoned.

(51) Int. Cl.
*C07K 14/28* (2006.01)
*C12N 15/74* (2006.01)

(52) U.S. Cl. .................. 536/23.7; 435/69.3; 435/252.33
(58) Field of Classification Search ........................ None
See application file for complete search history.

(56) References Cited

U.S. PATENT DOCUMENTS

| 4,328,209 | A | | 5/1982 | Finkelstein et al. |
|---|---|---|---|---|
| 4,666,837 | A | | 5/1987 | Harford et al. |
| 4,935,364 | A | | 6/1990 | Kaper et al. |
| 5,182,109 | A | | 1/1993 | Tamura et al. |
| 5,427,788 | A | * | 6/1995 | Rappuoli et al. ......... 424/190.1 |
| 5,601,827 | A | | 2/1997 | Collier et al. |
| 5,668,255 | A | | 9/1997 | Murphy |
| 5,770,203 | A | | 6/1998 | Burnette et al. |
| 5,874,287 | A | * | 2/1999 | Burnette et al. .......... 435/252.3 |

(Continued)

FOREIGN PATENT DOCUMENTS

EP 0396964 11/1990

(Continued)

OTHER PUBLICATIONS

Mekalanos, John J. et al, Nature, Dec. 1981, pp. 551-557, vol. 306(5943).*

(Continued)

*Primary Examiner*—Mark Navarro
*Assistant Examiner*—Ginny Portner
(74) *Attorney, Agent, or Firm*—Helen Lee; Otis Littlefied

(57) ABSTRACT

An immunogenic detoxified protein comprising the amino acid sequence of subunit A of a cholera toxin (CT-A) or a fragment thereof or the amino acid sequence of subunit A of an *Escherichia coli* heat labile toxin (LT-A) or a fragment thereof wherein the amino acids at, or in positions corresponding to Ser-63 and Arg-192 are replaced with another amino acid. The immunogenic detoxified protein is useful as vaccine for *Vibrio cholerae* or an enterotoxigenic strain of *Escherichia coli* and is produced by recombinant DNA means by site-directed mutagenesis.

10 Claims, 6 Drawing Sheets

U.S. PATENT DOCUMENTS

Figure 1:
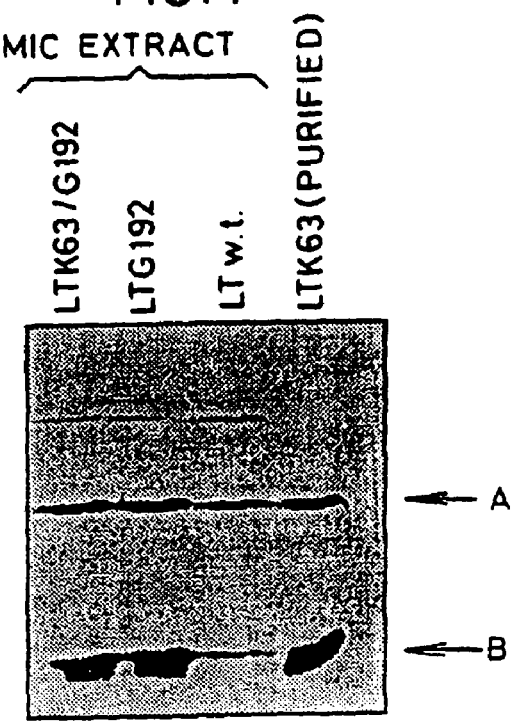
Figure 6:
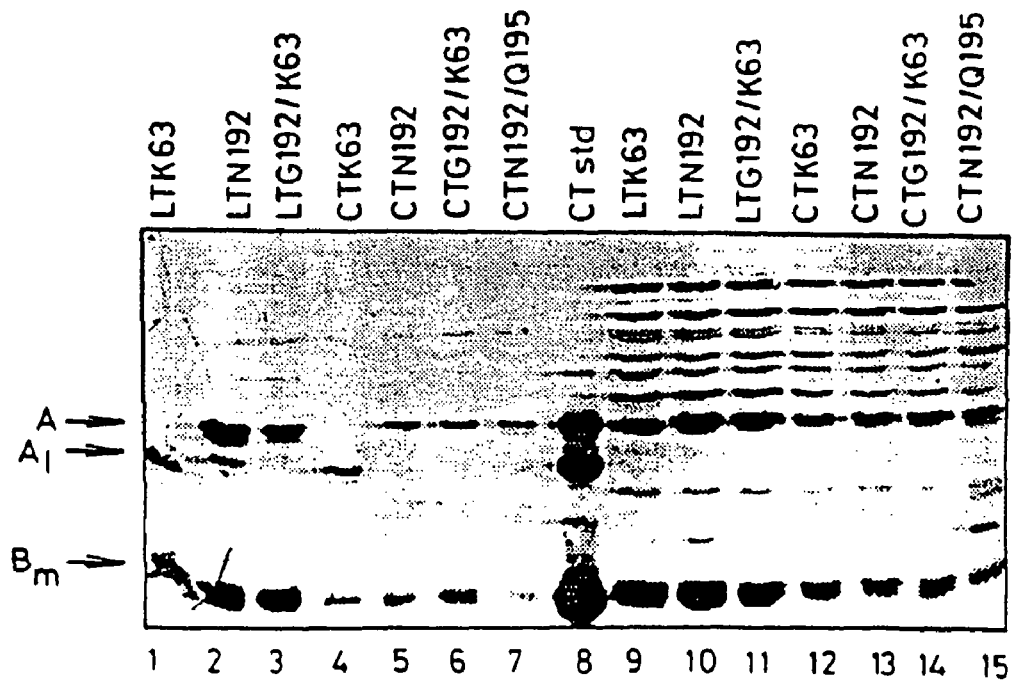
Figure 2A:
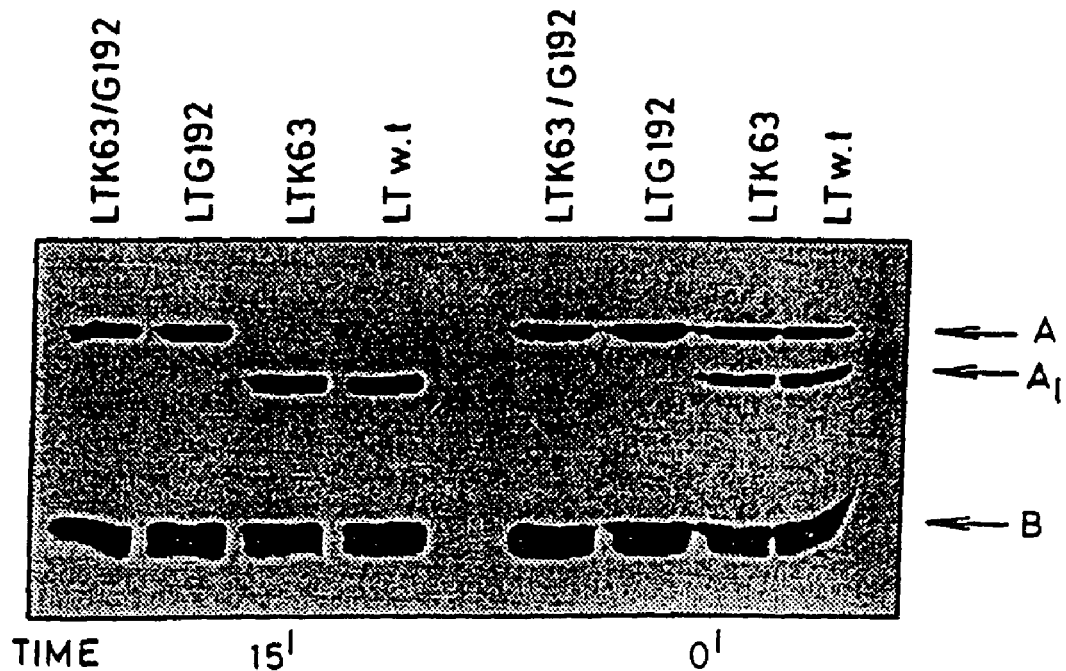
Figure 2B:
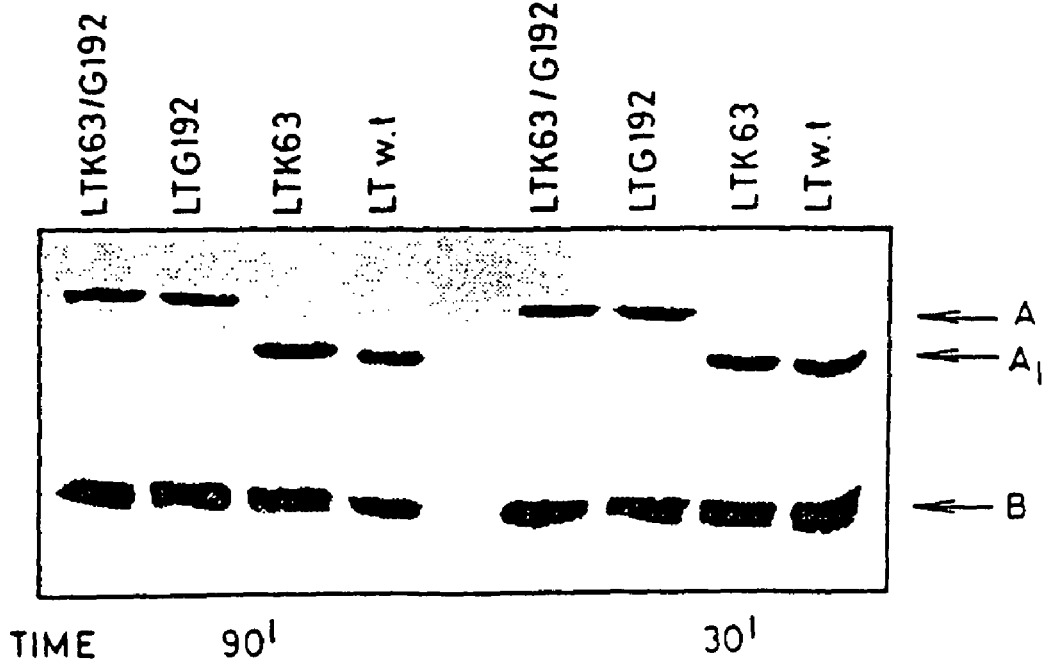
Figure 3A:
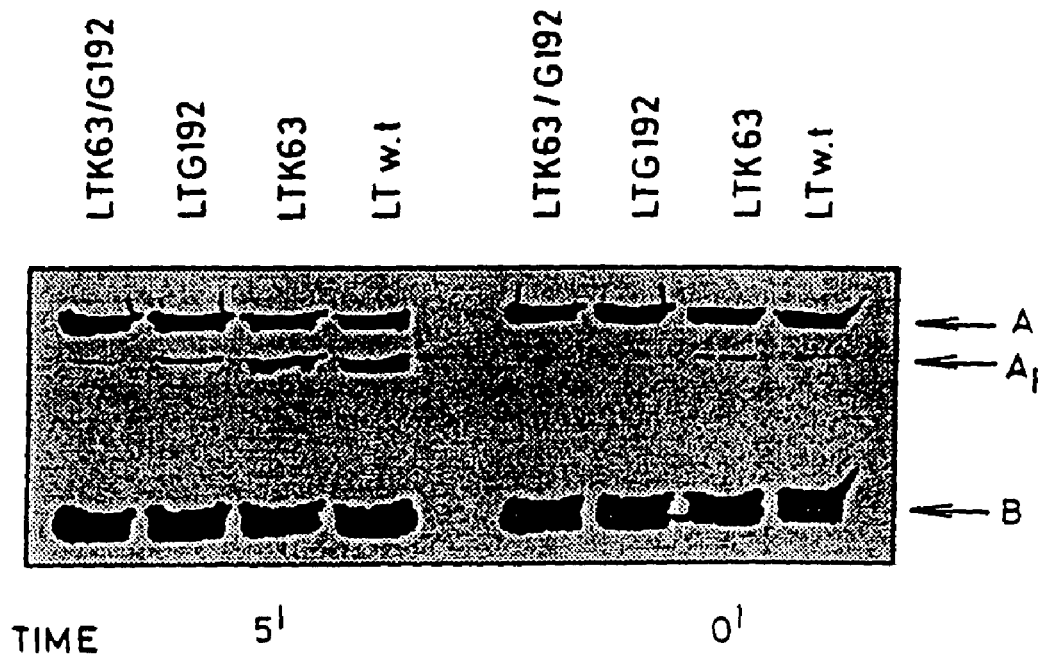
Figure 3B:
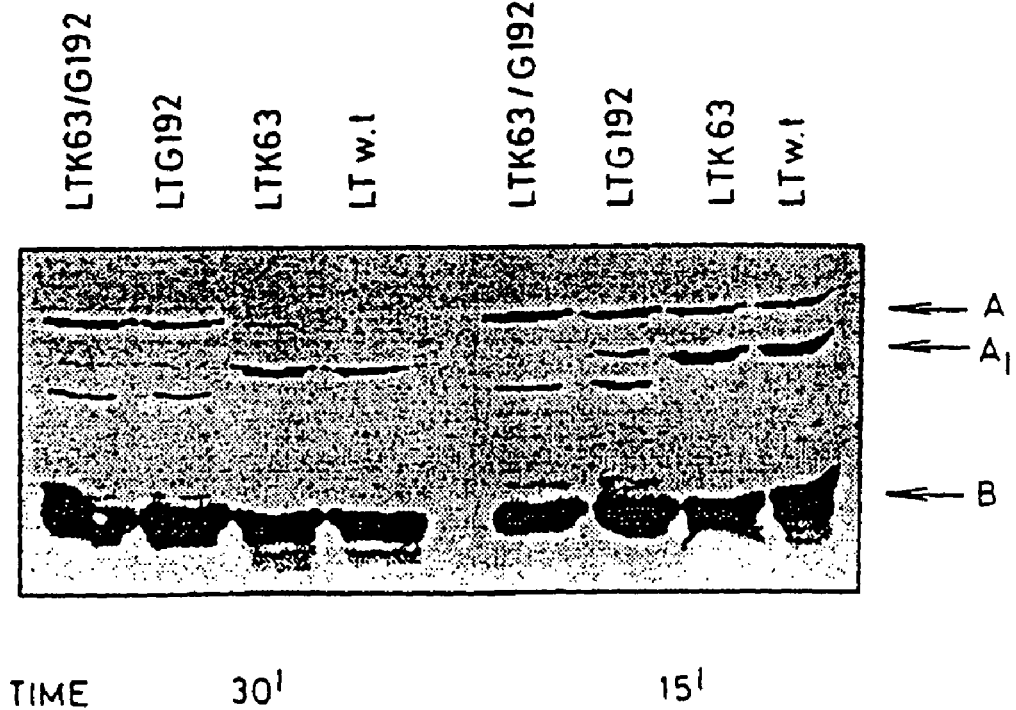
Figure 3C:
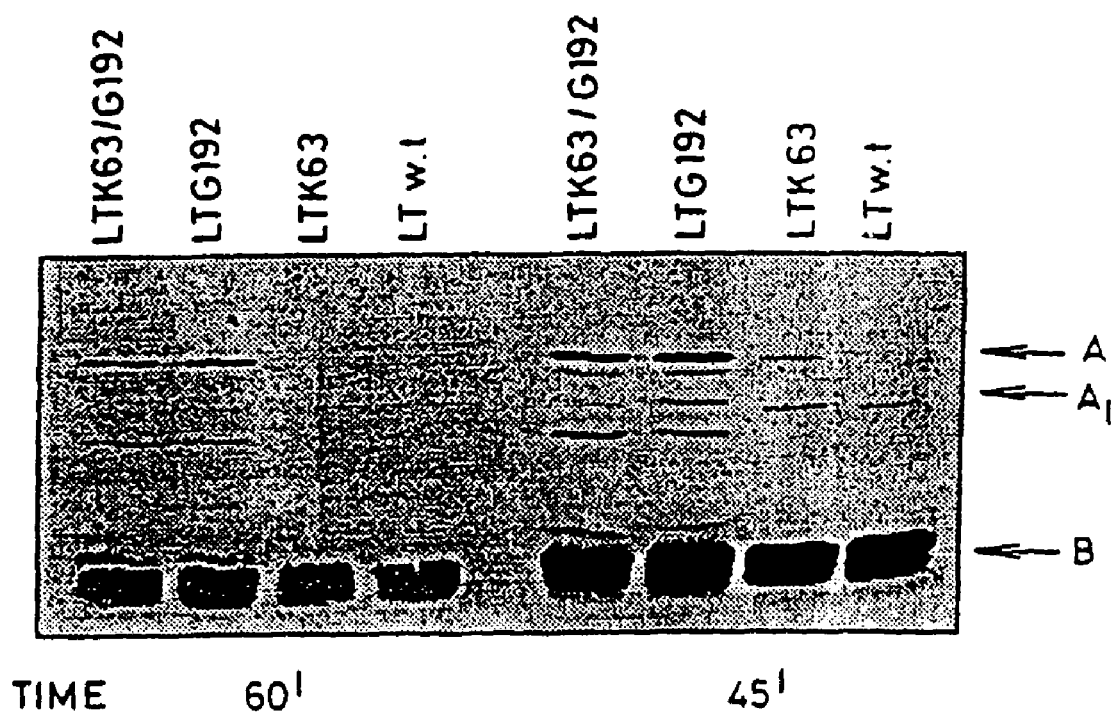
Figure 4:
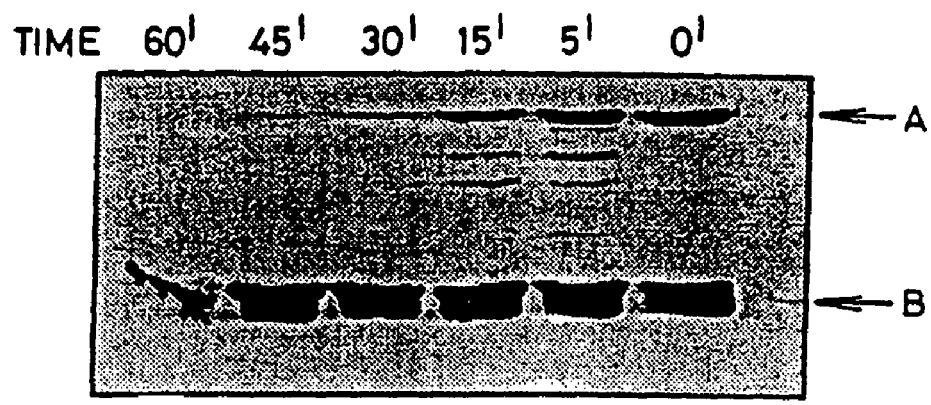
Figure 5:
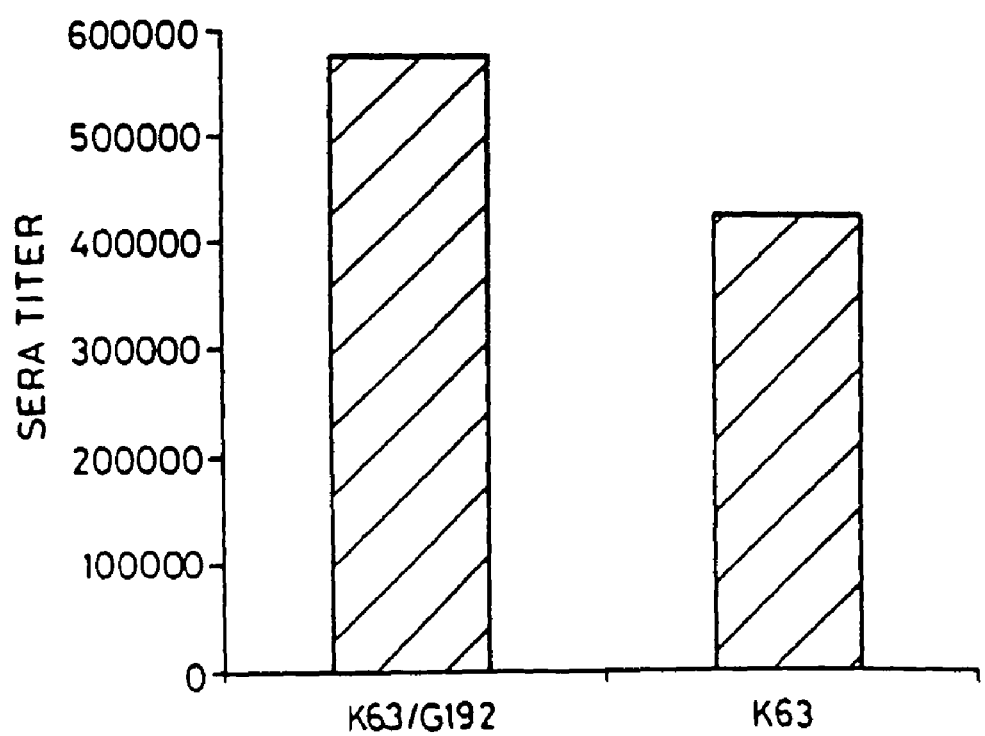
Figure 7:
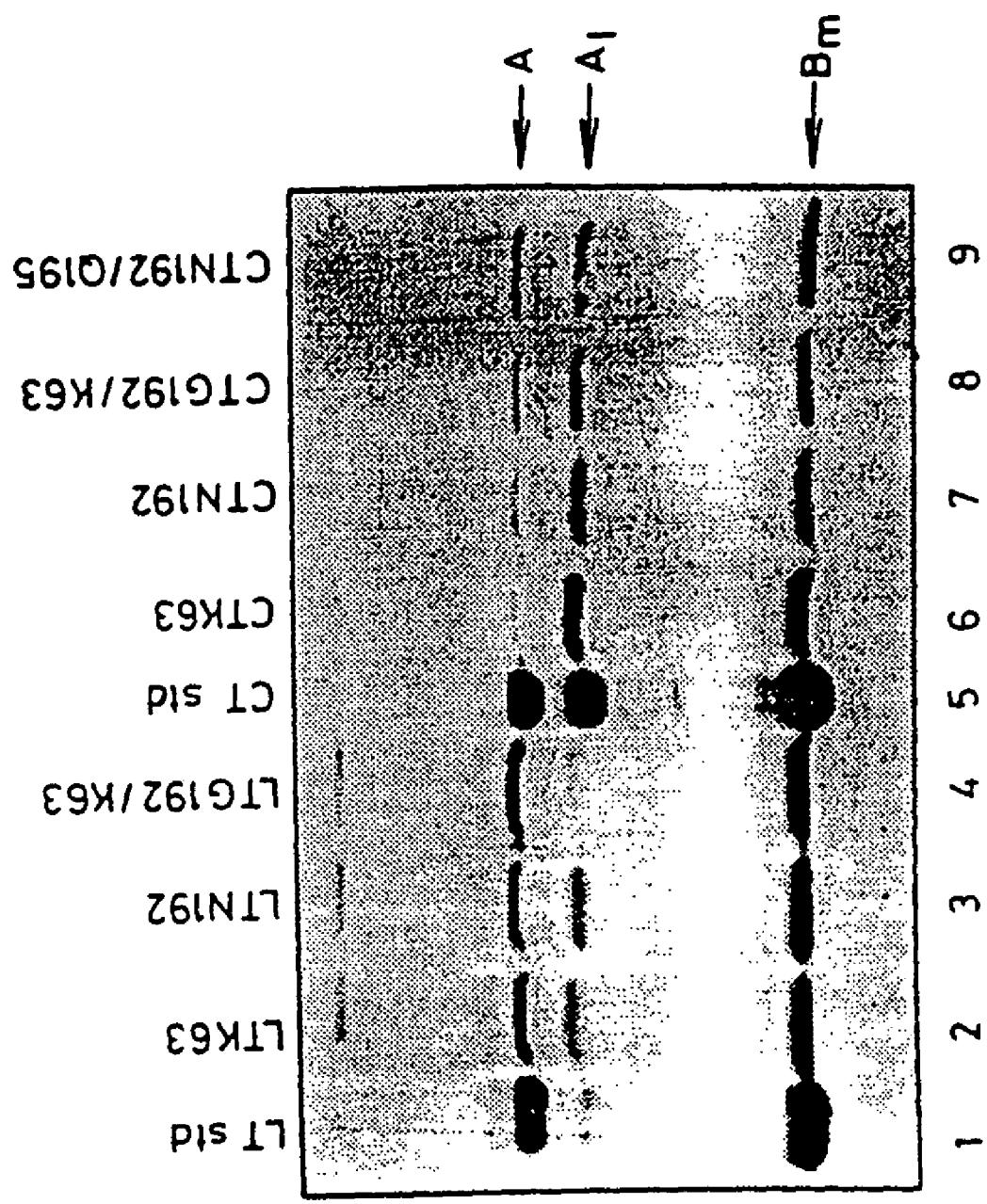

| | | | | |
|---|---|---|---|---|
| 6,019,982 | A | * | 2/2000 | Clements et al. ......... 424/236.1 |
| 6,033,673 | A | | 3/2000 | Clements |
| 6,149,919 | A | * | 11/2000 | Domenighini et al. ... 424/236.1 |
| 6,413,523 | B1 | * | 7/2002 | Clements ................. 424/241.1 |
| 6,436,407 | B1 | * | 8/2002 | Clements et al. ......... 424/208.1 |
| 6,440,423 | B1 | * | 8/2002 | Clements et al. ......... 424/236.1 |
| 7,056,521 | B2 | * | 6/2006 | Barchfeld et al. ........ 424/236.1 |
| 7,063,852 | B2 | * | 6/2006 | Clements ................. 424/203.1 |
| 7,070,781 | B2 | * | 7/2006 | Rappuoli ................. 424/184.1 |
| 7,115,730 | B1 | * | 10/2006 | Pizza et al. ................ 536/23.7 |
| 7,285,276 | B2 | * | 10/2007 | Murdin et al. ........... 424/185.1 |
| 7,332,174 | B2 | * | 2/2008 | Green et al. ............. 424/261.1 |
| 7,384,640 | B1 | * | 6/2008 | Holmes et al. ........... 424/201.1 |
| 7,632,513 | B2 | * | 12/2009 | Pizza et al. ............... 424/236.1 |
| 2002/0044939 | A1 | * | 4/2002 | Pizza et al. ............... 424/184.1 |
| 2003/0113345 | A1 | * | 6/2003 | Clements ................. 424/203.1 |
| 2003/0176653 | A1 | * | 9/2003 | Mason et al. ............... 530/350 |
| 2004/0137017 | A1 | * | 7/2004 | Pizza et al. ............... 424/261.1 |
| 2004/0176571 | A1 | * | 9/2004 | Green et al. ................ 530/350 |
| 2004/0181036 | A1 | * | 9/2004 | Green et al. ................ 530/350 |
| 2005/0106178 | A1 | * | 5/2005 | O'Hagan ................. 424/209.1 |
| 2005/0186266 | A1 | * | 8/2005 | Murdin et al. ............... 424/450 |
| 2006/0008476 | A1 | * | 1/2006 | Pizza et al. ............... 424/250.1 |
| 2006/0051378 | A1 | * | 3/2006 | Guidice et al. ........... 424/241.1 |
| 2006/0057155 | A1 | * | 3/2006 | Masignani et al. ....... 424/190.1 |
| 2006/0140981 | A1 | * | 6/2006 | Jonsdottir ................. 424/244.1 |
| 2006/0251675 | A1 | * | 11/2006 | Hagen ..................... 424/203.1 |
| 2008/0063665 | A1 | * | 3/2008 | Oster et al. .............. 424/232.1 |
| 2008/0112965 | A1 | * | 5/2008 | Murdin et al. ........... 424/190.1 |

FOREIGN PATENT DOCUMENTS

| | | |
|---|---|---|
| EP | 0462534 | 12/1991 |
| GB | 9320454.3 | 10/1994 |
| GB | 9324743.5 | 10/1994 |
| WO | WO 92/19265 | 11/1992 |
| WO | 93/13202 | * 7/1993 |
| WO | WO 93/13202 | 7/1993 |
| WO | WO 95/09649 | 4/1995 |
| WO | WO 95/34323 | 12/1995 |
| WO | WO 96/06627 | 3/1996 |
| WO | WO 99/58145 | 11/1999 |
| WO | WO 00/18434 | 4/2000 |

OTHER PUBLICATIONS

Pizza et al, Mol. Microbiology, Oct. 1994, pp. 51-60, vol. 14(1).*
Fontana, Maria Rita et al, Infection and Immunity, vol. 63(6), pp. 2356-2360, Jun. 1995.*
Clement et al, reference of record.*
Grant et al, Infection and Immunity, vol. 62(10), pp. 4270-4278, Oct. 1994.*
Fontana, Maria Rita et al, Infection and Immunity, vol. 63(6), pp. 2356-2360, Jun. 1995, Construction of Nontoxic Derivatives of Cholera toxin and Characterizatio not the Immunological Response against the A subunit.*
Boslego, J.W. et al., Vaccines and Immunotherapy, Chapter 17, 1991, 211-223.
Burnette, W.N. et al., "Site-specific mutagenesis of the catalytic subunit of cholera toxin: substituting lysine for arginine 7 causes loss of activity," *Inf. & Immun.*, 1991, 59:4266-4270.
Dallas, W.S. et al., "Cistrons encoding *Escherichia coli* heat-labile toxin," *J. Bacteriol.*, 1979, 139:850-858.
Dente, L. et al., "pEMBL: a new family of single stranded plasmids," *Nucleic Acids Res.*, 1983 11(6):1645-1655.
Domenighini, M. et al., "Identification of errors among database sequence entries and comparison of correct amino acid sequences for the heat-labile enterotoxins of *Eschericia coli* and *Vibrio cholerae*," *Mol. Microbial.*, 1995, 15(6):1165-1167.
Domenighini, M. et al., "Common features of the DNA-binding and catalytic site of ADP-ribosylating toxins," *Mol. Microbiol.*, 1994, 14(1):41-50.

Dickinson, B. et al., "Dissociation of *Escherichia coli* heat-labile enterotoxin adjuvanticity from ADP-ribosyltransferase activity," *Infection and Immunity*, 1995, 63(5):1617-1623.
Donta, S., "Detection of heat-labile *Escherichia coli* enterotoxin with the use of adrenal cells in tissue culture," *Science*,1974, 183:334-336.
Fontana, M.R. et al., "Construction of nontoxic derivatives of cholera toxin and characterization of the immunological response against the A subunit," *Infection and Immunity*, 1995, 63(6):2356-2360.
Grant, C. et al., "Role of trypsin-like cleavage at arginine 192 in the enzymatic and cytotonic activities of *Escherichia coli* heat-labile enterotoxin," *Infection and Immunity*, 1994, 62(10):4270-4278.
Grant, C.C.R. et al., "Effect of single amino acid changes on the ADP-ribosyltransferase activity of *Escherichia coli* heat-labile toxin subunit A," $92^{nd}$ *Gen. Meet. Am. Soc. Microbiol.*, 1992, Abstract B278, 74.
Harford, S. et al., "Inactivation of the *Escherichia coli* heat-labile enterotoxin by in vitro mutagenesis of the A-subunit gene," *Eur. J. Biochem.*, 1989, 183:311-316.
Hase, C. et al., "Construction and characterization of recombinant *Vibrio cholerae* strains producing inactive cholera toxin analogs," *Infection and Immunity*, 1994, 62(8):3051-3057.
Hirst, T. et al., "Transient entry of enterotoxin subunits into the periplasm occurs during their secretion from *Vibrio cholerae*," *J. Bacteriol.*, 1987, 169(3):1037-1045.
Holmgren, J. et al., "Oral immunization against cholera," *Curr. Top. Microbiol. Immunol.*, 1998, 146:197-204.
Jobling, M.G. et al., "Analysis of the structure and function of cholera toxin A subunit," *Abstr. Gen. Meet. Am. Soc. Microbiol.*, 1991, 91(0), 59, #B205.
Kaslow, H.R. et al., "Effects of site-directed mutagenesis on cholera toxin A1 subunit ADP-ribosyltransferase activity," $92^{nd}$ *Gen. Meet. Am. Soc. Microbiol.*, 1992, Asbract B291, 74.
Kaslow, H.R. et al., "Site-specific mutagenesis of the pertussis toxin S1 subunit gene: effects of amino acid substitutions involving residues 50-58," *Vaccine Research*, 1992, 1(1):47-54.
Lai, C.Y. et al., "Location and amino acid sequence around the ADP-ribosylation site in the cholera toxin active subunit $A_1$," *Biochem. Biophys. Res. Comm.*, 1983, 116:341-348.
*The Lancet*, Sep. 27, 1986, 328(8509):722-723, "Oral Cholera Vaccines".
Lebacq-Verheyden, A.M. et al., "Posttranslation processing of endogenous and of baculovirus-expressed human gastrin-releasing peptide precursor," *Mol. Cell. Biol.*, 1988, 8:3129-3135.
Lobet, Y. et al., "Effect of site-directed mutagenic alterations on ADP-ribosyltransferase activity of the A subunit of *Escherichia coli* heat-labile enterotoxin," *Inf. & Immun.*, 1991, 59:2870-2879.
Loosemore, S.M. et al., "Engineering of genetically detoxified pertussis toxin analogs for development of a recombianant whooping cough vaccine," *Infection and Immunity*, 1990, 58(11):3653-3662.
Lycke, N. et al., "The adjuvant effect of *Vibrio cholerae* and *Escherichia coli* heat-labile enterotoxins is linked to their ADP-ribosyltransferase activity," *Eur. J. Immunol.*, 1992, 22:2277-2281.
Magagnoli, C. et al., "Mutations in the A subunit affect yield, stability, and protease sensitivity of nontoxic derivatives of heat-labile enteroxotin," *Infection and Immunity*, 1996, 64(12):5434-5438.
Mekalanos, J.J. et al., "Cholera toxin genes: nucleotide sequence, deletion analysis and vaccine development," *Nature*, 1983, 306:551-557.
*Molecular Microbiology*, 1995, 15(6):1165-1167, "MicroCorrespondence".
Okamoto, J. et al., "Effect of substitution of glycine for arginine at position 146 of the A1 subunit on biological activity of *Escherichia coli* heat-labile enterotoxin," *Bacteriol.*, 1988, 2208.
Oseasohn, R., "Cholera," In Plotkin S.A., Mortimer, E.A. (Eds.), *Vaccines*, 1988, WB Saunders Co., Philadelphia, PA.
Pearson, G. et al., "Molecular cloning of *Vibrio cholerae* enterotoxin genes in *Escherichia coli* K-12," *Proc. Natl. Acad. Sci. USA*, 1982, 79:2976-2980.
Pickett, C.L. et al., "Genetics of type IIa heat-labile enterotoxin of *Escherichia coli*: operon fusions, nucleotide Sequence, and hybridization studies," *J. Bacteriol.*, 1987, 169:5180-5187.

Pizza, M. et al., "A genetically detoxified derivative of heat-labile *Escherichia coli* enterotoxin induces neutralizing antibodies against the A subunit," *J. Exp. Med.*, 1994, 180:2147-2153.

Pizza, M. et al., "Probing the structure-activity relationship of *Escherichia coli* LT-A by site-directed mutagenesis," *Mol. Microbiol.*, 1994, 14(1):51-60.

Pizza, M. et al., "The subunit S1 is important for pertussis toxin secretion," *J. Biol. Chem.*, 1990, 265(29):17759-17763.

Pronk, S. et al., "Heat-labile enteroxotin of *Escherichia coli*," *J. Biol. Chem.*, 1985, 260(25):13580-13584.

Rappuoli, R. et al., Structure and evolutionary aspects of ADP-ribosylating toxins, *Sourcebook of Bacterial Toxins*, 1991, Academic Press Limited, 1-21.

Sandkvist, M. et al., "Assembly of *Escherichia coli* heat-labile enterotoxin and its secretion from *Vibrio cholerae*," *Molecular Meachanisms of Bacterial Virulence*, 1993, Chapter 21, 293-309.

Sixma, T.K. et al., "Crystal structure of a cholera toxin-related heat-labile enterotoxin from *E. coli*," *Nature*, 1991, 351:371-377.

Spicer et al., "Sequence homologies between A subunits of *Escherichia coli* and *Vibrio cholerae* enterotoxins," *Proc. Natl. Acac. Sci. USA*, 1981, 78(1):50-54.

Spicer et al., "*Escherichia coli* heat-labile enterotoxin," *Biol. Chem.*, 1982, 257:5716-5721.

Tsuji, T. et al., "A simple amino acid substitution in the A subunit of *Escherichia coli* enterotoxin results in a loss of its toxic activity," *J. Biol. Chem.*, 1990, 265:22520-22525.

Yamamoto, T. et al., "Primary structure of heat-labile enterotoxin produced by *Escherichia coli* pathogenic for humans," *J. Biol. Chem.*, 1984, 259:5037-5044.

Zoller, M. et al., "Oligonucleotide-directed mutagensis using M13-derived vectors: an efficient and general procedure for the production of point mutations in any fragment of DNA," *Nucleic Acids Res.*, 1982, 10(20):6487-6500.

Burnette, "The Advent of Recombinant Pertussis Vaccines." *Biotechnol.* 8:1002-1005 (1990).

Burnette, *Vaccine Research & Developments* Marcel Dekker Inc,. New York, New York (1992).

Clements, et al., "Adjuvant Activity of *Escherichia Coli* Heat-Labile Enterotoxin and Effect on the Induction of Oral Tolerance in Mice to Unrelated Protein Antigens," *Vaccine* 6:269-277 (1988).

Communication to EPO Concerning Replacement Claim for Filing with the EPO in Application No. 99922284.7 (2003).

de Haan, et al., "Mutational Analysis or the Role of ADP-Ribosylation Activity in the Adjuvant Properties of the *Escherichia coli* Heat-Labile Enterotoxin Towards Intranasally Administered Keyhole Limpet Hemocyanin." *Eur. J. Immunol.* 28:1243-1250 (1998).

Del Guidice, et al., "Genetically Derived Toxoids for use as Vaccines and Adjuvants." *Vaccine* 17:S44-S52 (1999).

Douce, et al., "Mutants of *Escherichia coli* Heat-Labile Toxin Lacking ADP-Ribosyltransferase Activity act as Nontoxic, Mucosal Adjuvants." *PNAS USA* 92:1644-1648 (1995).

Douce et al., "Intranasal Immunogenicity and Adjuvanticity of Site Directed Mutant Derivatives of Cholera Toxin." *Infect. Immun.* 65:2821-2828 (1997).

EPO Communication pursuant to Article 96(2) EPC relating to Application EP No. 94928455.8-2116 (2001).

"Multicomponent Vaccine Development." *NIH Guide* vol. 22, No. 28 (1993).

Green, Bruce, Curriculum Vitae, 2005.

Hagen, Michael, Curriculum Vitae, 2005.

Hagiwar, et al., Effectiveness and Safety of Mutant *Escherichia coli* Heat-Labile Enterotoxin (LT H44A) as an Adjuvant for Nasal Influenza Vaccine. *Vaccine* 19:2071-2079 (2001).

Hartman, et al., "Native and Mutant Forms of Cholera Toxin and Heat-Labile Enterotoxin Effectively Enhance Protective Efficacy of Live Attenuated and Heat-Killed Shigella Vaccines." *Infect. Immun.* 67:5841-5847 (1999).

Hazama et al.,"Intranasal Immunization Against Herpes Simiplex Virus Infection by using a Recombinant Glycoprotein D Fused with Immunomodulating Proteins, the B Subunit of *Escherichia coli* Heat-Labile Enterotoxin and Interleukin-2." *Immunology* 78:643-649 (1993).

Hirst, et al., "Cholera Toxin and Related Enterotoxins as Potent Immune Modulators." *J. Appl. Microb. Symp. Suppl.* 48:26S-34S (1998).

Hirst, *The Comprehensive Sourcebook of Bacterial Protein Toxins*, Chapter 6, Academic Press, pp. 104-130, (1999).

Holmgren, et al., "Cholera Toxin and Cholera B Subunit as Oral-Mucosal Adjuvant and Antigen Vector Systems." *Vaccine* 11:1179-1184 (1993).

Lycke, et al., "Strong Adjuvant Properties of Cholera Toxin on Gut Mucosal Immune Responses to Orally Presented Antigens." *Immunol.* 56:301-308 (1986).

Lycke, et al, "The Mechanism of Cholera Toxin Adjuvanticity." *Res. Immunol.* 198:504-520 (1997).

Martindale, *Royal Pharmaceutical Society of Britain* Pharmaceutical Press, London, England, pp. 1277-1304(1993).

Rappouli, et al., "Structure and Mucosal Adjuventicity of Cholera and *Escherichia coli* Heat-Labile Enterotoxins." *Immunol. Today* 20:493-500 (1999).

Spangler, "Structure and Function of Cholera Toxin and The Related *Escherichia coli* Heat-Labile Enterotoxin." *Microbiol. Rev.* 56:622-647 (1992).

Streatfield, et al. , "Intermolecular Interactions Between the A and B Subunits of Heat-Labile Enterotoxin from *Escherichia coli* Promote Holotoxin Assembly and Stability In Vivo." *PNAS USA* 89:12140-12144 (1992).

*The Comprehensive Sourcebook of Bacterial Protein Toxins*, $2^{nd}$ Ed., Academic Press, pp. 696-697, 2001.

Tsuji, et al., "Relationship Between a Low Toxicity of the Mutant A Subunit of Enterotoxigenic *Escherichia coli* Enterotoxin and its Strong Adjuvant Action." *Immunology* 90:176-182 (1997).

Verweij, et al.,Mucosal Immunoadjuvant Activity of Recombinant *Escherichia coli* Heat-Labile Enterotoxin and its B Subunit: Induction of Systematic IgG and Secretory IgA Responses in Mice by Intranasal Immunization with Influenza Virus Surface Antigen. *Vaccine* 16:2069-2076 (1998).

Walker, et al., "Use of Heat-Labile Toxin Enterotoxigenic *Escherichia coli* to Facilitate Mucosal Immunization." *Vaccine Res.* 2:1-10 (1993).

Williams, Neil, Affidavit, Curriculum Vitae, and Annex 1, 2005.

Yamamoto, et al., "Mutants in the ADP-Ribosyltransferase Cleft of Cholera Toxin Lack Diarrheagenicity but Retain Adjuvanticity." *J. Exp. Med.* 185:1203-1210 (1997).

\* cited by examiner

TIME 5' 0'

TIME 30' 15'

IMMUNOGENIC DETOXIFIED MUTANTS OF CHOLERA TOXIN

This application is a continuation of application Ser. No. 10/611,398 filed Jun. 30, 2003 (now U.S. Pat. No. 7,632,513), which is a continuation of application Ser. No. 09/819,917 filed Mar. 28, 2001 (now abandoned). U.S. application Ser. No. 09/819,917, is a continuation of application Ser. No. 08/981,208 filed Dec. 22, 1997 (now abandoned), which is a national phase of PCT/IBM96/00703 filed Jul. 1, 1996. PCT/IB/96/00703 claims priority of GB No. 9513371.6 filed Jun. 30, 1995. All of the above applications are incorporated herein by reference in their entireties.

FIELD OF THE INVENTION

The present invention relates to immunogenic detoxified proteins of cholera toxins (CT), or of heat labile toxins (LT) produced by the enterotoxigenic strains of Escherichia coli (E. coli) wherein the amino acids at, or in positions corresponding to, Ser-63 and Arg-192 are replaced with another amino acid and to their use in vaccines which are useful for the prevention or treatment of cholera or enterotoxigenic E. Coli infections and as mucosal adjuvants for other immunogenic proteins. The detoxified, immunogenic proteins can be suitably produced using recombinant DNA by techniques by site-directed mutagenesis of DNA encoding the wild type toxins.

BACKGROUND TO THE INVENTION

Cholera is a contagious disease widely distributed in the world, in particular in the Third World, where, in certain areas, it is endemic. The serious disorders which develop in the intestinal system prove fatal in a high percentage of the recorded cases of the disease.

The etiological agent of cholera is the Gram-negative microorganism Vibrio cholerae (V. cholerae). This colonises the intestinal tract of individuals who have come into contact with it through ingestion of contaminated food or water, and multiplies to very high concentrations. The principal symptom is severe diarrhoea as a result of which the patient can lose as much as 10-15 litres of liquids per day via the faeces. As a result of the severe dehydration and loss of electrolytes, the patient does not withstand the infection in 50-60% of cases, and dies. The diarrhoea caused by V. cholerae is due to the secretion of cholera toxin, CT, which acts by stimulating the activity of the adenylate cyclase enzyme so as to induce disturbances at cell level.

Although cholera can be effectively cured by controlled and intense rehydration, the distribution of a vaccine in desirable with a view to complete control and future eradication of the disease.

At the present time, there exists a vaccination against cholera, consisting of parenteral administration of killed bacteria. Although some countries insist on vaccination against the disease, there are serious doubts as to its real usefulness, given that the current cellular vaccine protects against the consequences of the infection in only 50% of the cases and that the protection is also extremely limited in duration, to less than 6 months.

In Bangladesh, an experimental trial is in progress (1990-92) of an oral vaccine consisting of killed bacteria with the addition of subunit B of cholera toxin, which is known to be highly immunogenic. This product succeeds in inducing lasting protection, without special side effects (Holmgren J., Clemens J., Sack D A., Sanchez J. and Svennerholm A M; "Oral Immunization against cholera" Curr. Top. Microbiol. Immunol. (1988), 146, 197-204).

Cholera toxin resembles the heat labile toxins of enterotoxigenic strains of Escherichia coli in amino acid sequence, structure and mode of action.

The consequences of infection with an enterotoxigenic strain of E. coli are similar to, though less serious than, those of cholera, and consist of severe diarrhoea and intestinal disorders.

The CT and LT toxins all comprise a single A subunit (or protomer A) responsible for the enzymic activity of the toxin (herein CT-A or LT-A) and five identical B subunits (or protomer B) which are involved in the binding of the toxin to the intestinal epithelial cells (herein CT-B or LT-B).

The A subunit penetrates the cell membrane and causes activation of adenylate cyclase by NAD-dependent ADP-ribosylation of a GTP-binding protein which controls the activity of the enzyme. The clinical effect of this is to cause massive fluid loss into the intestine.

Considerable research has been conducted on cholera toxin and the E. coli heat labile toxins.

The sequence of CT is known and has been described (Mekalanos J. J. et al. Nature 306, page 551 (1983)).

The sequence of LT from enterotoxigenic strains of E. coli is, as mentioned, 80% homologous to CT and it too is known and described in the scientific literature. Spicer E. K. et al (Biol. Chem. 257 p. 5716-5721 (1982)) describe the amino acid sequence of the A sub unit of the heat labile toxin from an enterotoxigenic strain of E. coli found in pigs.

A bacterial chromosomal form of LT has been identified and sequenced by Pickett C. L. et al. (J. Bacteriol. 169, 5180-5187, (1987).

The sequence of the A subunit of LT from a strain of E. coli known to affect humans has also been sequenced (Yamamoto et al, J. Biol. Chem., 259, 5037-5044, (1984)).

In view of the potential clinical significance of a vaccine against cholera and enterotoxigenic bacteria there is a continuing and great interest in producing a detoxified toxin capable of immunising against cholera and enterotoxigenic bacteria. The techniques of genetic engineering allow specific mutations to be introduced into the genes encoding the toxins id the production of the mutated toxins using now conventional techniques of gene expression and protein purification.

Various groups have attempted to identify mutations of the genes, which involve loss of the toxicity characteristics of the encoded proteins. The studies are predominantly being carried out in respect of the gene for the toxin LT, from E. coli.

Harford, S. et al. (Eur. J. Biochem. 183, page 311 (1989)) describe the production of a toxoid by in vitro mutagenesis of the LT-A gene from E. coli pathogenic for pigs. The resulting successful mutation contained a Ser-61-Phe substitution and a Gly-79-Lys substitution, the former being considered the more important. Harford et al. suggest that, because of the similarities between the LT-A genes in E. coli pathogenic to humans and pigs and the CT-A gene, and because the toxins are thought to operate by a common mechanism, it may be possible to produce a cholera holotoxoid by introducing the Ser-61-Phe mutation into the CT-A gene.

Tsuji, T. et al. (J. Biol. Chem. 265, p. 22520 (1990)) describe the mutation of the LT-A gene from plasmid EWD299 to produce a single substitution Glu-112-Lys which affects the toxicity of the mutant LT yet does not change the immunogenicity of the protein.

Grant, C. C. R. et al. (Abstract B289 of the 92nd General Meeting of the American Society for Microbiology, 26-30th May 1992) describe conservative substitutions of histidines at 44 and 70 and tryptophan at 127 in LT-A which result in significant reductions in enzymic activity.

Some work has been conducted on mutations to CT.

Kaslow, H. R. et al. (Abstract B291 of the 92nd General Meeting of the American Society for Microbiology, 26-30th May 1992) describe mutating Asp-9 and His-44 and truncating after amino acid 180 in CT-A which all essentially eliminate activity. Mutating Arg-9 is said to markedly attenuate activity. Mutating other amino acid sites had little effect on toxicity.

Burnette, W. N. et al. (Inf. and Immun. 59(11), 4266-4270, (1991)) describe site-specific mutagenesis of CT-A to produce an Arg-7-Lys mutation paralleling that of a known detoxifying mutation in the A subunit of the *Bordetella pertussis* toxin. The mutation resulted in the complete abolition of detectable ADP-ribosyltransferase activity.

International patent application WO 92/19265 (Burnette, Kaslow and Amgen Inc.) describes mutations of CT-A at Arg-7, Asp-9, Arg-11, His-44, His-70 and Glu-112.

Mutations at Glu-110 (LT and CT) and Arg-146 (LT) have also been described in the literature (Lobet, Inf. Immun., 2870, 1991; Lai, Biochem. Biophys. Res. Comm. 341 1983; Okamoto J. Bacteriol. 2208, 1988).

The crystal structure of LT has been determined by Sixma et al (Nature, 351, 371-377, May 1991) and confirms the mutatagenesis results described earlier in the literature, explaining structurally the significance of Glu-112 and Ser-61 in activity of the A sub unit and suggesting that His-244, Ser-114 and Arg-54 which are in the immediate neighbourhood may be important for catalysis or recognition.

It is known that the development of toxicity of the A subunits of CT and LT requires proteolytic cleavage of A1 and A2 subunits at around amino acid Arg-192 (Grant et al Inf. & Immun. (1994) 62(10) 4270-4278).

Immunogenic detoxified proteins comprising the amino acid sequence of subunit A of a cholera toxin (CT-A) or a fragment thereof or subunit A of an *Escherichia coli* heat labile toxin (LT-A) or a fragment thereof, wherein one or more amino acids at, or in positions corresponding to Val-53, Ser-63, Val-97, Tyr-104 or Pro-106 are replaced with another amino acid are disclosed in WO 93/13202 (Biocine Sclavo SpA). optionally the amino acid sequence may include other mutations such as, for example, substitutions at one or more of Arg-7, Asp-9, Arg-11, His-44, Arg-54, Ser-61, His-70, His-107, Glu-110, Glu-112, Ser-114, Trp-127, Arg-146 or Arg-192.

Detoxified mutants of pertussis toxin have been reported to be useful both for direct intranasal vaccination and as a m mucosal adjuvant for other vaccines (Roberts et al. Inf. & Immun. (1995) 63(6) 2100-2108). Published International patent application WO 95/17211 (Biocine SpA) describes the use of detoxified mutants of CT and LT as mucosal adjuvants.

SUMMARY OF THE INVENTION

We have discovered that a double mutation of the CT or LT amino acid sequence results in a immunogenic detoxified protein with improved stability characteristics. Although we have previously shown that mutation at Ser-63 detoxifies CT and LT, further experiments have shown, unexpectedly that mutation around the, Arg-192 position markedly improves the stability of the resulting protein. Protein stability is a critical factor in the design of active agents for use in vaccines since the half-life of such an agent correlates with the efficacy of the vaccine. Longer lived agents provide better vaccination offering the possibility of reducing the need for adjuvants or even shortening the vaccination regimen. Similarly, stability affects the efficacy of an active agent present in a composition for its adjuvant activity.

According to the present invention, there is provided an immunogenic detoxified protein comprising the amino acid sequence of subunit A of a cholera toxin (CT-A) or a fragment thereof or the amino acid sequence of subunit A of an *Escherichia coli* heat labile toxin (LT-A) or a fragment thereof wherein the amino acids at, or in positions corresponding to, Ser-63 and Arg-192 are replaced with another amino acid.

In this specification, references to CT and LT encompass the various naturally occurring strain variants as well other variants encompassing changes from the sequences disclosed herein which do not affect the immunogenicity of the assembled toxoid.

The amino acid sequences for CT and LT are definitively described in Domenighini et al. Molecular Microbiology (1995) 15(6) 1165-1167.

The amino acid substituted for the wild type amino acid may be a naturally occurring amino acid or may be a modified or synthetic amino acid, provided that the mutant retains the necessary immunogenic properties and exhibits a substantially reduced toxicity. The substitution may involve deletion of an amino acid.

Substitutions which alter the amphotericity and hydrophilicity whilst retaining the steric effect of the substituting amino acid as far as possible are generally preferred.

As used herein, the term "detoxified" means that the immunogenic composition exhibits a substantially lower toxicity relative to its naturally occurring toxin counterpart. The substantially lower toxicity should be sufficiently low for the protein to be used in an immunogenic composition in an immunologically effective amount as a vaccine with causing significant side effects. For example, the immunogenic detoxified protein should have a toxicity of less than 0.01% of the naturally occurring toxin counterpart. The toxicity may be measured in mouse CHO cells or preferably by evaluation of the morphological changes induced in Y1 cells. The term "toxoid" means a genetically detoxified toxin.

The immunogenic protein may be a CT or LT subunit A toxoid, but is preferably an assembled toxin molecule comprising a mutated CT-A or LT-A subunit and five B subunits of CT or LT. The B subunit may be a naturally occurring subunit or may itself be mutated.

The immunogenic protein is preferably a naturally occurring CT-A or an LT-A suitably modified as described above. However, conservative amino acid changes may be made which do not affect the immunogenicity or the toxicity of immunogenic protein and preferably do not affect the ability of the immunogenic protein to form complete toxin with B subunit protein. Also, the immunogenic protein may be a fragment of CT-A or an LT-A provided that the fragment is immunogenic and non toxic and contains at least one of the conserved regions containing one of the mutations according to the invention.

Both positions Ser-63 and Arg-192 are modified in the detoxified protein of the invention. Preferably, Ser-63 is replaced with Lys-63. Preferably Arg-192 is replaced with Asn-192 or Gly-192. Most preferably Ser-63 is replaced with Lys-63 and Arg-192 is replaced with Asn-192 or Gly-192.

According to a second aspect of the invention, there is provided an immunogenic composition for use as a vaccine comprising an immunogenic detoxified protein of the first aspect of the invention and a pharmaceutically acceptable carrier.

The invention also provides a vaccine composition comprising an immunogenic detoxified protein according to the first aspect of the invention and a pharmaceutically acceptable carrier. The vaccine composition may further comprise an adjuvant. Alternatively, the vaccine composition may comprise a second antigen capable of raising an immunological response to another disease. In such an alternative composition, the immunogenic detoxified protein acts as a mucosal adjuvant.

According to a third aspect of the invention, there is provided a method of vaccinating a mammal against *Vibrio cholerae* or an enterotoxigenic strain of *Escherichia coli* comprising administering an immunologically effective amount of an immunogenic detoxified protein according to the first aspect of the invention. Optionally, the immunogenic detoxified protein of the invention may act as an adjuvant for a second immunogenic protein administered separately, sequentially or with the immunogenic detoxified protein of the invention.

The immunogenic detoxified proteins of the invention may be synthesised chemically using conventional peptide synthesis techniques, but are preferably produced by recombinant DNA means.

According to a fourth aspect of the invention there is provided a DNA sequence encoding an immunogenic detoxified, protein according to the first aspect of the invention.

Preferably the DNA sequence contains a DNA sequence encoding a complete CT or LT comprising DNA encoding both the detoxified subunit A and subunit B in a polycistronic unit. Alternatively, the DNA may encode only the detoxified subunit A.

According to a fifth aspect of the invention, there is provided a vector carrying a DNA according to the fourth aspect of the invention.

According to a sixth aspect of the invention, there is provided a host cell line transformed with the vector according to the fifth aspect of the invention.

The host cell may be any host capable of producing CT or LT but is preferably a bacterium, most suitably *E. coli* or *V. cholerae* suitably engineered to produce the desired immunogenic detoxified protein.

In a further embodiment of the sixth aspect of the invention, the host cell may itself provide a protective species, for example an *E. coli* or *V. cholerae* strain mutated to a phenotype lacking wild type LT or CT and carrying and expressing an immunogenic detoxified protein of the first aspect of the invention.

In a further embodiment of the sixth aspect of the invention the host cell is capable of expressing a chromosomal LT-A gene according to the first aspect of the invention.

According to a seventh aspect of the invention, there is provided a process for the production of an immunogenic detoxified protein according to the first aspect of the invention comprising culturing a host cell according to the sixth aspect of the invention.

According to a eighth aspect of the invention there is provided a process for the production of DNA according to the fourth aspect of the invention comprising the steps of subjecting a DNA encoding a CT-A or an LT-A or a fragment thereof to site-directed mutagenesis.

According to a ninth aspect of the invention there is provided a process for the formulation of a vaccine comprising bringing an immunogenic detoxified protein according to the first aspect of the invention into association with a pharmaceutically acceptable carrier and optionally with an adjuvant.

INDUSTRIAL APPLICABILITY

The immunogenic detoxified protein of the invention constitutes the active component of a vaccine composition useful for the prevention and treatment of cholera infections or infections by enterotoxigenic strains of *E. coli*. The immunogenic detoxified protein may also be used in a vaccine composition as a mucosal adjuvant. The compositions are thus applicable for use in the pharmaceutical industry.

BRIEF DESCRIPTION OF THE DRAWINGS

FIG. 1 Western blot of periplasmic extracts of *E. coli* TG1 strains expressing wild-type LT, LTG192 or LTK63/G192 mutants, showing the A and B subunits. Purified LTK63 has been used as control.

FIG. 2 Western blot of purified wild-type LT and LTK63, LTG192, LTK63/G192 mutants treated with trypsin at 37° C. at the initial time, after 15, 30 and 90 minutes, respectively. (Toxin-trypsin ratio is 1:100, incubation buffer TEAN pH 7.5).

FIG. 3 Western blot of purified wild-type LT and LTK63, LTG192, LTK63/G192 mutants treated with trypsin at the initial time, after 5, 15, 30, 45, 60 minutes, respectively. (Toxin-trypsin ratio 1:100, incubation buffer TEAN pH 7.5±3.5M urea.)

FIG. 4 Western blot of purified LTN192 mutant treated with trypsin at the initial time, 5, 15, 30, 45, 60 minutes, respectively. (Toxin-trypsin ratio 1:100, incubation buffer TEAN pH 7.5±3.5M urea).

FIG. 5 Titers of anti-LT IgG in the sera of mice after 36 days of immunization with 1 μg of LTK63 and LTK63/G192, respectively. Four mice from each group were immunized i.n. with LTK63 or LTK63/G192. Sera of each group were pooled and samples tested. Titers were determined as the reciprocal of dilution corresponding to $OD_{450}$=0.3.

FIG. 6 Western blot showing the expression in *E. coli* of CT and LT mutants into the proteolytic loop and analysis of resistance to trypsin treatment. Lane 1, 2, 3, 4, 5, 6, 7, periplasmic extract of *E. coli* expressing LT and CT mutants treated with 13.5 μg/ml of trypsin at 37° C. for 15 min. Lane 8, CT purified. Lane 9, 10, 11, 12, 13, 14, 15, periplasmic extract of *E. coli* expressing CT and LT mutants untreated. An uncleaved A subunit of LT and CT molecule; A1, cleaved A subunit; Bm, B monomer.

FIG. 7 Western blot showing the expression in 0395 *V. cholerae* strain of CT and LT mutants into the proteolytic loop to test the resistance at the specific protease (hemagglutinin/protease). Lane 1, LT purified. Lane 2, 3, 4, supernatant of *V. cholerae* 0395 expressing LT mutants. Lane 5, CT purified. Lane 6, 7, 8, 9, supernatant of *V. cholerae* 0395 expressing CT mutants. An uncleaved A subunit of LT and CT molecule; A1, cleaved A subunit; Bm, B monomer.

DETAILED DESCRIPTION OF EMBODIMENTS OF THE INVENTION

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed., 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I-IV (D. M. Weir and C. C. Blackwell eds. 1986).

Standard abbreviations for nucleotides and amino acids are used in this specification. All publications, patents, and patent applications cited herein are incorporated by reference.

In particular, the following amino acid abbreviations are used:

| Alanine | A | Ala |
| Arginine | R | Arg |
| Asparagine | N | Asn |
| Aspartic Acid | D | Asp |
| Cysteine | C | Cys |
| Glycine | G | Gly |
| Glutamic Acid | E | Glu |
| Glutamine | Q | Gln |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

As mentioned above examples of the immunogenic detoxified protein that can be used in the present invention include polypeptides with minor amino acid variations from the natural amino acid sequence of the protein other than at the sites of mutation specifically mentioned.

A significant advantage of producing the immunogenic detoxified protein by recombinant DNA techniques rather than by isolating and purifying a protein from natural sources is that equivalent quantities of the protein can be produced by using less starting material than would be required for isolating the protein from a natural source. Producing the protein by recombinant techniques also permits the protein to be isolated in the absence of some molecules normally present in cells. Indeed, protein compositions entirely free of any trace of human protein contaminants can readily be produced because the only human protein produced by the recombinant non-human host is the recombinant protein at issue. Potential viral agents from natural sources and viral components pathogenic to humans are also avoided. Also, genetically detoxified toxin are less likely to revert to a toxic from than more traditional, chemically detoxified toxins.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes) and inactive virus particles. Such carriers are well known to those of ordinary skill in the art. Additionally, these carriers may function as immunostimulating agents (adjuvants).

Preferred adjuvants to enhance effectiveness of the composition include, but are not limited to: aluminum salts (alum) such as aluminium hydroxide, aluminium phosphate, aluminium sulfate etc., oil emulsion formulations, with or without other specific immunostimulating agents such as muramyl peptides or bacterial cell wall components, such as for example (1) MPS9 (Published International patent application WO-A-90/14837, containing 5% Squalene, 0.5% Tween® 80, 0.5% Spans 85 (optionally containing various amounts of MTP-PE (see below), although not required) formulated into submicron particles using a microfluidizer such as Model 110Y microfluidizer (Microfluidics, Newton, Mass. 02164), (2) SAF, containing 10% squalene, 0.4% Tween 80, 5% pluronic-blocked polymer L121, and thr-MDP (see below) either microfluidized into a submicron emulsion or vortexed to generate a larger particle size emulsion, and (3) RIBI™ adjuvant system (RAS) (Ribi Immunochem, Hamilton, Mont.) containing 2% Squalene, 0.2% Tweens 80 and one or more bacterial cell wall components from the group consisting of monophosphoryl lipid A (MPL), trehalose dimycolate (TDM), and cell wall skeleton (CWS) preferably MPL+CWS (Detox™), muramyl peptides such as N-acetyl-muramyl-L-threonyl-D-isoglutamine (thr-MDP), N-acetyl-normuramyl-L-alanyl-D-iso-glutamine (nor-MDP), N-acetylmuramyl-L-alanyl-D-isoglutaminyl-L-alanine-2-(1'-2'dipalmitoyl -sn-glycero-3-hydroxyphosphoryloxy)-ethylamine (MTP-PE) etc., and cytokines, such as interleukins (IL-1, IL-2 etc) macrophage colony stimulating factor (M-CSF), tumour necrosis factor (TNF) etc. Additionally, saponin adjuvants, such as Stimulon™ (Cambridge Bioscience, Worcester, Mass.) may be used or particles generated therefrom such as ISCOMS (immunostimulating complexes). Furthermore, Complete Freunds Adjuvant (CFA) and Incomplete Freunds Adjuvant (IFA) may be used. Alum and MF59 are preferred.

The immunogenic detoxified protein of the invention may used as an adjuvant for a second antigen in an immunologically active composition for the treatment or vaccination of the human or animal body.

The immunogenic compositions (e.g. the antigen, pharmaceutically acceptable carrier and adjuvant) typically will contain diluents, such as water, saline, glycerol, ethanol, etc. Additionally, auxiliary substances, such as wetting or emulsifying agents, pH buffering substances, and a the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect as discussed above under pharmaceutically acceptable carriers.

Immunogenic compositions used as vaccines comprise an immunologically effective amount of the antigenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g. by injection either subcutaneously or intramuscularly. Additional formulations suitable for other modes of administration include oral and pulmonary formulations, suppositories and transdermal applications. Dosage treatment may be a single dose schedule or a multiple dose schedule. The vaccine may be administered in conjunction with other immunoregulatory agents.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well. as unmodified forms of the polynucleotide.

A "replicon" is any genetic element, e.g., a plasmid, a chromosome, a virus, a cosmid, etc. that behaves as an autonomous unit of polynucleotide replication within a cell; i.e., capable of replication under its own control. This may include selectable markers.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and may also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

"PCR" refers to the technique of polymerase chain reaction as described in Saiki, et al., Nature 324:163 (1986); and Scharf et al., Science (1986) 233:1076-1078; and U.S. Pat. No. 4,683,195; and U.S. Pat. No. 4,683,202.

As used herein, x is "heterologous" with respect to y if x is not naturally associated with y in the identical manner; i.e., x is not associated with y in nature or x is not associated with y in the same manner as is found in nature.

"Homology" refers to the degree of similarity between x and y. The correspondence between the sequence from one form to another can be determined by techniques known in the art. For example, they can be determined by a direct comparison of the sequence information of the polynucleotide. Alternatively, homology can be determined by hybridization of the polynucleotides under conditions which form stable duplexes between homologous regions (for example, those which would be used prior to $S_1$ digestion), followed by digestion with single-stranded specific nuclease(s), followed by size determination of the digested fragments.

As used herein, the term "polypeptide" refers to a polymerof amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3-5 amino acids, and more preferably at least 8-10 amino acids, and even more preferably at least 11-15 amino acids, or which is immunologically identifiable with a polypeptide encoded in the sequence. This terminology also includes a polypeptide expressed from a designated nucleic acid sequence.

The protein may be used for producing antibodies, either monoclonal or polyclonal, specific to the protein. The methods for producing these antibodies are known in the art.

"Recombinant host cells", "host cells," "cells," "cellcultures," and other such terms denote, for example, microorganisms, insect cells, and mammalian cells, that canbe, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Examples for mammalian host cells include Chinese hamster ovary (CHO) and monkey kidney (COS) cells.

Specifically, as used herein, "cell line," refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells. Preferably, cell lines include nonhybrid cell lines or hybridomas to only two cell types.

As used herein, the term "microorganism" includes prokaryotic and eukaryotic microbial species such as bacteria and fungi, the latter including yeast and filamentous fungi.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

By "genomic" is meant a collection or library of DNA molecules which are derived from restriction fragments that have been cloned in vectors. This may include all or part of the genetic material of an organism.

By "cDNA" is meant a complementary DNA sequence that hybridizes to a complementary strand of DNA.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

Once the appropriate coding sequence is isolated, it can be expressed in a variety of different expression systems; for example those used with mammalian cells, baculoviruses, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual.* 2nd ed.].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberta et al. (1989) *Molecular Biology of the Cell,* 2nd ed.]. Enhancer elements derived from viruses may be particularly useful, because they usually have a broader host range. Examples include the SV40 early gene enhancer [Dijkema et al. (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) Science 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminater/polyadenylation signals include those derived from SV40 [Sambrook et al. (1989)

"Expression of cloned genes in cultured mammalian cells." In *Molecular Cloning: A Laboratory Manual]*.

Some genes may be expressed more efficiently when introns (also called intervening sequences) are present. Several cDNAs, however, have been efficiently expressed from vectors that lack splicing signals (also called splice donor and acceptor sites) [see e.g., Gothing and Sambrook (1981) *Nature* 293:620]. Introns are intervening noncoding sequences within a coding sequence that contain splice donor and acceptor sites. They are removed by a process called "splicing," following polyadenylation of the primary transcript [Nevins (1983) *Annu. Rev. Biochem.* 52:441; Green (1986) *Annu. Rev. Genet.* 20:671; Padgett et al. (1986) *Annu. Rev. Biochem.* 55:1119; Krainer and Maniatis (1988) "RNA splicing." In *Transcription and splicing* (ed. B. D. Hames and D. M. Glover)].

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a procaryotic host for cloning and amplification. Examples of such mammalian-bacteria shuttle vectors include pMT2 [Kaufman et al. (1989) *Mol. Cell. Biol.* 9:946 and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art.

Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No. 1555* (1987) (hereinafter "Summers and Smith").

Prior to inserting the DNA sequence encoding the protein into the baculovirus genome, the above described components, comprising a promoter, leader (if desired), coding Sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a procaryotic ampicillin-resistance (amp) gene and origin of replication for selection and propagation in *E. Coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene Ad encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene*, 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 31:592; human gastrin-releasing peptide, Lebacq-Verheyden et al., (1988), *Molec. Cell. Biol.* 8:3129; human IL-2, Smith et al., (1985) *Proc. Nat'l. Acad. Sci. USA,* 8:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or po protein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 1:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and ' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 µm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti , Autographa californica, Bombyx mori, Drosophila melanogaster, Spodoptera frugiperda,* and *Trichoplusia ni* (PCT Pub. No. WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See. e.g., Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Bacterial Systems

Bacterial expression techniques are known in the art. A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) (Raibaud et al. (1984) *Annu. Rev. Genet.* 18:173). Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EPO Publ. Nos. 036 776 and 121 775]. The g-lactamase (bla) promoter system [Weissmann (1981) "The cloning of interferon and other mistakes." In *Interferon* 3 (ed. I. Gresser), bacteriophage lambda PL [Shimatake et al. (1981) *Nature* 292:128] and TS [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophase T7 RNA polymerase/promoter system is an example of a coupled promoter system [Studier et al. (1986) *J. Mol. Biol.* 189:113; Tabor et al. (1985) *Proc. Natl. Acad. Sci.* 82:1074]. In addition, a hybrid promoter can also be comprised of a bacteriophage promoter and an *E. coli* operator region (EPO Publ. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34). The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual]*.

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO Publ. No. 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810). Fusion proteins can also be made with sequences from the lacZ [Jia et al. (1987) *Gene* 60:197], trpE [Allen et al. (1987) *J. Biotechnol.* 5:93; Makoff et al. (1989) *J. Gen. Microbiol*, 135:11], and Chev [EPO Publ. No. 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipultation of Gene Expression*; Ghrayeb et al. (1984) *EMBO J.* 3:2437] and the *E. coli* alkaline phosphatase signal sequence (phoA) [Oka e al. (1985) *Proc. Natl. Acad. Sci.* 82:7212]. As an additional example, the signal sequence of the alpha-amylase gene from various Bacillus strains can be used to secrete heterologous proteins from *B. subtilis* [Palva et al. (1982) *Proc. Natl. Acad. Sci. USA* 79:5582; EPO Publ. No. 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a procaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (EPO Publ. No. 127 328). Integrating vectors may also be comprised of bacteriophage or transposon sequences.

Usually, extrachromosomal and integrating expression constructs may contain selectable markers to allow for the selection of bacterial strains that have been transformed.

Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia the following bacteria: *Bacillus subtilis* [Palva et al. (1982) *Proc. Natl. Acad. Sci. USA* 79:5582; EPO Publ. Nos. 036 259 and 063 953; PCT Publ. No. WO 84/04541], *Escherichia coli* [Shimatake et al. (1981) *Nature* 292:128; Amann et al. (1985) *Gene* 40:183; Studier et al. (1986) *J. Mol. Biol.* 189:113; EPO Publ. Nos. 036 776, 136 829 and 136 9073, *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with CaCl$_2$ or other agents, such as divalent cations and DMSO. DNA can also be introduced into bacterial cells by electroporation. Transformation procedures usually vary with the bacterial species to be transformed. See e.g., [Masson et al. (1989) *FEMS Microbiol. Lett.* 60:273; Palva et al. (1982) *Proc. Natl. Acad. Sci. USA* 79:5582; EPO Publ. Nos. 036 259 and 063 953; PCT Publ. No. WO 84/04541, *Bacillus], [Miller et al. (*1988) *Proc. Natl. Acad. Sci.* 85:856; Wang et al. (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem.* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) *Infec. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

iv. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EPO Publ. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Publ. No. 329 203). The yeast PROS gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes i the Yeast Saccharomyces cerevisiae," in: *Plasmids of Medical Environmental and Commercial Importance* (eds. K>N>Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial A expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EPO Publ. No. 196 056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (see, e.g., PCT Publ. No. WO 88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EPO Publ. No. 012 873; JPO Publ. No. 62,096,086) and the A-factor gene (U.S. Pat. No. 4,588,684). Alternatively, leaders of non-yeast origin, such as an interferon leader, exist that also provide for secretion in yeast (EPO Publ. No. 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EPO Publ. No. 324 274). Additional leaders employing an alpha-factor leader fragment that provides for secretion include hybrid alpha-factor leaders made with a presequence of a first yeast, but a pro-region from a second yeast alphafactor. (See e.g., PCT Publ. No. WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two S replication systems, thus allowing it to be maintained, for example, in yeast for expression and in a procaryotic host for cloning and amplification. Examples of such yeast-bacteria shuttle vectors include YEp24 [Botstein et al. (1979) Gene 8:17-24], pCl/1 [Brake et al. (1984) Proc. Natl. Acad. Sci. USA 81:4642-4646], and YRp17 [Stinchcomb et al. (1982) J. Mol. Biol. 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See e.g., Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) Methods in Enzymol. 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) Proc. Natl. Acad. Sci. USA 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) Microbiol, Rev. 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter a, the following yeasts: Candida albicans [Kurtz, et al. (1986) Mol. Cell. Biol. 6:142], Candida maltose [Kunze, et al. (1985) J. Basic Microbiol. 25:141], Hansenula polymorpha [Gleeson, et al. (1986) J. Gen. Microbiol. 132:3459; Roggenkamp et al. (1986) Mol. Gen. Genet. 202:302], Kluyveromyces fragilis [Das, et al. (1984) J. Bacteriol. 158:1165], Kluyveromyces lactis [De Louvencourt et al. (1983) J. Bacteriol. 154:737; Van den Berg et al. (1990) Bio/Technology 8:135], Pichia guillerimondii [Kunze et al. (1985) J. Basic Microbiol. 25:1411, Pichia pastoris [Cregg, et al. (1985) Mol. Cell. Biol. 5:3376; U.S. Pat. Nos. 4,837,148 and 4,929,555], Saccharomyces cerevisiae [Hinnen et al. (1978) Proc. Natl. Acad. Sci. USA 75:1929; Ito et al. (1983) J. Bacteriol. 153:163], Schizosaccharomyces pombe (Beach and Nurse (1981)

Nature 300:706], and *Yarrowia lipolytica* (Davidow, et al. (1985) *Curr. Genet.* 10:380-471 Gaillardin, et al. (1985) *Curr. Genet,* 10:49).

Methods of introducing exogenous DNA into yeast hosts are well-known in the art, and usually include either the transformation of spheroplasts or of intact yeast cells treated with alkali cations. Transformation procedures usually vary with the yeast species to be transformed. See e.g., [Kurtz et al. (1986) *Mol. Cell. Biol.* 6:142; Kunze et al. (1985) *J. Basic Microbiol.* 25:141; *Candida*]; [Gleeson et al. (1986) *J. Gen. Microbiol.* 132:3459; Roggenkamp et al. (1986) *Mol. Gen. Genet.* 202:302; Hansenula]; [Das et al. (1984) *J. Bacteriol.* 158:1165; De Louvencourt et al. (1983) *J. Bacteriol.* 154: 1165; Van den Berg et al. (1990) *Bio/Technology* 8:135; *Kluyveromyces*]; [Cregg et al. (1985) *Mol. Cell. Biol.* 5:3376; Kunze et al. (1985) *J. Basic Microbiol.* 25:141; U.S. Pat. Nos. 4,837,148 and 4,929,555; *Pichia*]; [Hinnen et al. (1978) *Proc. Natl. Acad. Sci. USA* 75;1929; Ito et al. (1983) *J. Bacteriol.* 153:163 *Saccharomyces*]; [Beach and Nurse (1981) *Nature* 300:706; *Schizosaccharomyces*]; [Davidow et al. (1985) *Curr. Genet.* 10:39; Gaillardin et al. (1985) *Curr. Genet.* 10:49; *Yarrowia*].

1. Preparation of LT mutants 1.1. Source of LT DNA

The 2 kb SmaI-HindIII fragment from plasmid pEWD299, containing the LT genes and the LT promoter region (Pronk et al., 1985; Spicer et al., 1981), was subcloned into the Blue-Script KS vector (Stratagene, San Diego, Calif.) generating the BS-LT and was used in all subsequent studies.

1.2. Methods of Mutation

Site-directed mutagenesis was performed on single-stranded

DNA, using the method of Zoller and Smith (Zoller and Smith, 1982). To introduce the G192 mutation, using the following oligonucleotide:

```
5'-AATTCATCAGGCACAATCACA-3'    (SEQ ID NO: 1)
``` was used. Single-stranded DNA from BS-LT and BS-LTK63 plasmids, containing the wild-type and the mutated 1.3kb SmaI-EcoRI fragment, respectively, were used to perform site-directed mutagenesis with G192-oligonucleotide.DNA manipulations were performed by standard procedures (Sambrook et al., 1989).

1.3. Expression and Purification of the Mutated Coding Region

LTG192 and LTK63/G192 mutants were purified from the periplasm of recombinant *E. coli* TG1 strains grown in a 20-liter fermentor. After centrifugation and sonication of the bacterial pellet, the purification was performed using CPG 350 (Controlled Pore Glass) (Sigma and Electronucleonics, St. Louis, USA), A5M Agarose (Biorad, Richmond, USA) and Sephacryl S-200 (Pharmacia, Uppsala, Sweden) columns, as described by Pronk et al. (Pronk et al., 1985). Purified proteins with a concentration ranging from 0.44 to 1.5 mg/ml were stored at 4° C. in the buffer TEAN pH 7.5.

2. Preparation of CT Mutants 2.1. Source of CT DNA

The 1. 1 kb fragment of pJM17 plasmid (Pearson, G.D.N., et al., 1982), containing the ctxAB gene, was amplified by PCR technique using the following oligonucleotides:

```
                                        (SEQ ID NO: 2)
5' - GGCAGATTCTAGACCTCCTGATGAAATAAA - 3' (ctxA)
and
                                        (SEQ ID NO: 3)
5' - TGAAGTTTGGCGAAGCTTCTTAATTTGCCATACTAATTGCG -
3' (ctxB).
```

The amplified XbaI-HindIII fragment was subcloned in PEKBL 19 vector (Dente, L., et al. 1983 ) and used for site-directed mutagenesis (Zoller, M. J., et al. 1982 ).

2.2. Methods of Mutation

Single-stranded DNA of pEMBL 19-CT K63 plasmid, containing the 1.1 kb XbaI-HindIII fragment, mutated in position 63, was used to perform site-directed mutagenesis with G192 oligonucleotide:

```
AATGCTCCAGGCTCATCGATG.    (SEQ ID NO: 4)
```

2.3. Expression of the Mutated Coding Region

The mutated XbaI-HindIII fragment containing the two mutations (Ser63→Lys, Arg192→Gly) was subcloned under the control of CT promoter into pGEM-3 vector (Promega, Madison, USA), generating the pGEM-CTK63/G192. *E. coli* TG1 and *V. Cholerae* 0395-NT strains were transformed by electroporation (Sambrook, J., et al. 1989) with pGEM-CTK63/G192 plasmid. The mutant protein CTX63/G192 was expressed into the periplasm of *E. coli* strain and into the culture supernatant of *V. Cholerae* strain. The periplasmic extract of *E. coli* were prepared as described (Pizza M., et al. 1990).

3. Properties of LT Mutants 3.1. Toxicity Test

Toxin Activity on Y1 Cells.

The morphological change caused by LT on Y1 adrenal cells (Donta, S. T. et al., 1973) was used to detect the toxic activity of LT and LTG192 and LTK63/G192 mutants. The assay is was performed in microtiter plates using 50,000 cells/well. The results were read after 48 hr of incubation. The assay detected 5 pg/well of wild type toxin. The LTG192 mutant was toxic at 12 pg/well, the double mutant LTK63/G192 was non toxic at 11 μg.

Rabbit Ileal Loop Assay.

New Zealand adult rabbits (ca. 2.5 kg) were used for the assay. The rabbits were starved for 24 hrs before the experiment. Before the operation, the rabbits were anaesthetized and fixed on the operation table. The abdomen of the rabbit was opened with a scalpel and the intestine was extracted . The ceacum was searched and 20-30 cm from this tract of intestine, 12-14 loops were made (each 5-6 cm in length) up to the approximative end of the intestine towards the stomach. 1 ml of the sample was injected into the loop and then the abdomen was closed. After 18-20 hrs, the liquid accumulated in the loop was collected and measured with a syringe. The length of the loop was measured again. The results were expressed as liquid volume in loop length (ml/cm).

3.2. Immunogenicity Tests

The mucosal immunogenicity of LTK63 and LTK63/G192 was tested by immunizing four mice intranasally (i.n.) with 1 μg of LT K63 and LT K63/G192, respectively. For i.n. immunizations, proteins were resuspended in phosphate-buffered saline (pH7.2; PBS) and delivered in a volume of 30 μg (15 μl/nostril). All the animals were immunized on days 1, 22, 36 and responses were followed by test sample bleedings collect at days 0, 21 and 35. Mice were terminally bled on day 56.

Toxin-specific antibodies were measured using a GM1 capture ELISA. Antitoxin levels were estimated against the homologous antigen used in the immunization. The plates were coated with 100 µl/well of 1.5 µg/ml GM1 ganglioside (Sigma Chemical Co., St. Louis, USA) at 4° C. overnight. Plates were washed three times with PBS, 0.05% Tween 20 (PBS/T). 200 µl/well of 1% BSA were added and the plates were incubated for 1 hour at 37° C. 100 µl/well of the antigen were added and incubated overnight at 4° C. The sera of each mouse was add to each well starting from a dilution of 1:50 and subsequently 1:2 dilutions; serum samples were incubated for 2 hours at 37° C. Plates were washed as described above and incubated with anti-mouse immunoglobulin G conjugated to alkaline phosphatase (Sigma). After three washes, the substrate of alkaline phosphatase (pNPP) was added and the absorbancies were read at 450 nm. ELISA titers were determined arbitrarily as the dilution corresponding to OD450=0.3.

3.3. Stability Test

Trypsin treatment of LT and LT mutants. 60 µg of LT and of each mutant were treated with 0.60 µg of trypsin (Sigma, St. Louis, USA) (molar rate 100/1), in 300 µg final volume of TEAN pH7.5 (non denaturing conditions) or TEAN pH7.5±3.5M urea (denaturing conditions) at 37° C. Samples of 30 µl were collected at 0, 15, 30, 90 minutes (in non denaturing conditions) or 0, 5, 15, 30, 45, 60 minutes (in denaturing conditions) and the reaction stopped by addition of 10 µl of 4× electrophoresis sample buffer (20% dithiothreitol, Bio Rad Richmond, USA; 8% sodiumdodecylsulfate, Bio Rad, Richmond, USA; 40% glycerol RPE-ACS, Carlo Erba, Milan, Italy; 0.02% bromophenolblue, Bio Rad, Richmond, USA; in Tris/HCl 0.25M pH6.8, Sigma, St. Louis, USA) and heating to 95° C. for 5 minutes. The samples were run on 15% SDS-PAGE minigels and analysed by western blotting (Towbin et al., 1979 using rabbit anti-LT polyclonal antibody at a dilution of 1/300.

3.4. Conclusions

The results of the toxicity tests show that:

12 pg of the single mutant LTG192 are able to induce a toxic effect on Y1 cells, while 11 µg of the double mutant LTK63/G192 do not.

50 ng of LTG192 are able to induce a fluid accumulation in the intestinal loop of rabbits, while 100 µg of the double mutant do not.

In terms of immunogenicity, the titer of the anti toxin response in mice immunized with LTK63/G192 are greater then those observed in mice immunized with LTK63.

The double mutant LTK63/G192 is more resistant to proteolysis then the single mutant LT K63. The X subunit of LT and LTK63 is completely processed in $A_1$ and $A_2$ after 15 minutes of incubation with trypsin. The A subunit of LTG192 and LTK63/G192 is resistant to the trypsin at least after 90 minutes of incubation. Moreover, the A subunit of LTK63 is completely degraded after 60 minutes of incubation with trypsin in denaturing condition, while the A subunits of LTG192 and LTK63/G192 has been only partially digested after 60 minutes of incubation with trypsin in denaturing condition.

4. Properties of CT Mutants 4.1. Stability Test

Trypsin Treatment.

50 μl of periplasmic extract of *E. Coli* strain containing the CTK63/G192 mutant was treated with 13.5 μg/ml of trypsin at .37° C. for 15 min. After incubation at the sample were added of 4× loading buffer to stop the reaction.

30 μl of *V. Cholerae* culture supernatant and 30 μl of periplasmic extract of *E. coli* treated with trypsin and untreated were loaded on 15% SDS-Polyacrylamide gel and the proteins were transferred on nitrocellulose membrane to perform a Western blotting.

4.2. Conclusions

The results show that both the single mutant CTN192 and the double mutant CTK63/G192, are more resistant to proteases then the wild-type toxin. However, these mutants are still processed by the *V. cholerae* specific protease.

REFERENCES

Deute, L., G. Cesareni, and R. Cortese. 1983. pEMBL: a new family of single stranded plasmid. Nucleic. Acid. Res. 11: 1645-1655

Donta, B. T., H. W. Moon and S. C. Whipp. 1973. Detection and use of heat-labile *Escherichia coli* enterotoxin with the use of adrenal cells in tissue culture. Science (Wash. D.C.). 183:334

Pearson, G. D. N., and J. J. Mekalanos. 1982. Molecular cloning of *Vibrio cholerae* enterotoxin gene in *Escherichia coli* K-12. Proc. Natl. Acad. Sci. USA. 79: 2976-2980.

Pizza, M., A. Covacci, M. Bugnoli, R. Manetti and R. Rappuoli. 1990. The S1 subunit is important for pertussis toxin secretion. J. Biol. Chem. 265:17759-17763.

Pronk, S. E., H. Hofstra, H Groendijk, J. Kinqima, M. B. A. Swarte, F. Dorner, J. Drenth, W. G. J. Hol and B. Witholt. 1985. Heat-labile enterotoxin of *Escherichia coli: characterization of different crystal forms. J. Biol. Chem.* 260: 13580.

Sambrook, J., E. F. Fritsch and T. Maniatis. 1989. Molecular cloning. A laboratory manual. Cold Spring Harbor Laboratory Press, Cold Spring Harbor, N.Y.

Spicer, E. K., W. M. Kavanaugh, W. S. Dallas, S. Falkow, W. Konigsberg and D. Shafer. 1981. Sequence homologies between A subunits of *E. coli* and *V. cholerae* enterotoxins. Proc. Natl. Acad. Sci. USA. 78:50.

Zoller, M. J. and M. Smith. 1982. Oligonucleotide-directed mutagenesis using M13-derived vectors: an efficient and general procedure for the production of point mutations in any fragment of DNA. Nucleic Acids Res. 10:6487.

The invention claimed is:

1. A DNA molecule encoding an immunogenic detoxified protein which comprises the amino acid sequence of subunit A of a cholera toxin (CT-A) or the amino acid sequence of subunit A of an *Escherichia coli* heat labile toxin (LT-A) wherein the amino acid at the position corresponding to Ser-63 of the mature wild-type sequence is replaced with lysine and the amino acid at the position corresponding to Arg-192 of the mature wild-type sequence is replaced with glycine, and further wherein
   (i) the immunogenic detoxified protein is more resistant to trypsin proteolysis than wild type CT-A or LT-A;
   (ii) the immunogenic detoxified protein exhibits reduced toxicity as compared to a CT or LT subunit A protein in which only the amino acid residue Arg-192 is replaced with glycine; and
   (iii) the immunogenic detoxified protein exhibits enhanced immunogenicity as compared to a CT or LT subunit A protein in which the amino acid residue Ser-63 is replaced with lysine.

2. A vector carrying the DNA molecule according to claim 1.

3. A host cell line transformed with the vector according to claim 2.

4. The DNA molecule of claim 1, said molecule encoding an immunogenic detoxified protein which comprises the amino acid sequence of subunit A of a cholera toxin (CT-A).

5. The DNA molecule of claim 1, wherein the detoxified protein has a toxicity of less than 0.01% of the naturally occurring toxin counterpart.

6. The DNA molecule of claim 4, said DNA molecule further encoding for at least one CT subunit B.

7. The DNA molecule of claim 6, wherein said subunit A and said subunit B comprise a polycistronic unit.

8. The DNA molecule of claim 1, said DNA molecule further encoding for at least one LT subunit B.

9. The DNA molecule of claim 8, wherein said subunit A and said subunit B comprise a polycistronic unit.

10. A process for the production of the immunogenic detoxified protein of claim 1, comprising culturing a host cell expressing the DNA molecule of claim 1 and isolating the protein expressed by said DNA molecule.

* * * * *

SEQUENCE LISTING

<160> NUMBER OF SEQ ID NOS: 6

<210> SEQ ID NO 1
<211> LENGTH: 21
<212> TYPE: DNA

```
<213> ORGANISM: Artificial Sequence
<220> FEATURE:
<221> NAME/KEY: misc_feature
<223> OTHER INFORMATION: Primer

<400> SEQUENCE: 1
aattcatcag gcacaatcac a                                               21

<210> SEQ ID NO 2
<211> LENGTH: 30
<212> TYPE: DNA
<213> ORGANISM: Artificial Sequence
<220> FEATURE:
<221> NAME/KEY: misc_feature
<223> OTHER INFORMATION: Primer

<400> SEQUENCE: 2
ggcagattct agacctcctg atgaaataa a                                     30

<210> SEQ ID NO 3
<211> LENGTH: 41
<212> TYPE: DNA
<213> ORGANISM: Artificial Sequence
<220> FEATURE:
<221> NAME/KEY: misc_feature
<223> OTHER INFORMATION: Primer

<400> SEQUENCE: 3
tgaagtttgg cgaagcttct taatttgcca tactaattgc g                         41

<210> SEQ ID NO 4
<211> LENGTH: 21
<212> TYPE: DNA
<213> ORGANISM: Artificial Sequence
<220> FEATURE:
<221> NAME/KEY: misc_feature
<223> OTHER INFORMATION: Primer

<400> SEQUENCE: 4
aatgctccag gctcatcgat g                                               21

<210> SEQ ID NO 5
<211> LENGTH: 241
<212> TYPE: PRT
<213> ORGANISM: E. coli

<400> SEQUENCE: 5

Asn Asp Phe Phe Arg Ala Asp Ser Arg Thr Pro Asp Glu Ile Arg Gln
1               5                   10                  15

Ala Gly Gly Leu Leu Pro Arg Gly Gln Gln Glu Ala Tyr Glu Arg Gly
            20                  25                  30

Thr Pro Ile Asn Ile Asn Leu Tyr Glu His Ala Arg Gly Thr Val Thr
        35                  40                  45

Gly Asn Thr Arg His Asn Asp Gly Tyr Val Ser Thr Thr Val Thr Leu
    50                  55                  60

Arg Gln Ala His Leu Ile Gly Gln Asn Ile Leu Gly Ser His Asn Glu
65                  70                  75                  80

Tyr Tyr Ile Tyr Val Val Ala Pro Ala Pro Asn Leu Phe Asp Val Asn
                85                  90                  95

Gly Val Leu Gly Arg Tyr Ser Pro Tyr Pro Ser Glu Asn Glu Phe Ala
            100                 105                 110

Ala Leu Gly Gly Ile Pro Leu Ser Gln Ile Ile Gly Trp Tyr Arg Val
        115                 120                 125
```

Ser Phe Gly Ala Leu Glu Gly Met Gln Arg Asn Arg Asp Tyr Arg
130                 135                 140

Gly Asp Leu Phe Ser Gly Leu Thr Val Ala Pro Asn Ala Asp Gly Tyr
145                 150                 155                 160

Gln Leu Ala Gly Phe Pro Ser Asn Phe Pro Ala Trp Arg Glu Met Pro
                165                 170                 175

Trp Ser Thr Phe Ala Pro Glu Gln Cys Val Pro Asn Asn Lys Glu Phe
                180                 185                 190

Lys Ser Gly Val Cys Ile Ser Ala Thr Asn Val Leu Gly Lys Tyr Asp
                195                 200                 205

Leu Met Asn Phe Lys Lys Leu Leu Lys Arg Arg Leu Ala Leu Thr Phe
210                 215                 220

Phe Met Ser Asp Asp Phe Thr Gly Val His Gly Glu Lys Asp Glu
225                 230                 235                 240

Leu

<210> SEQ ID NO 6
<211> LENGTH: 236
<212> TYPE: PRT
<213> ORGANISM: E. coli

<400> SEQUENCE: 6

Asn Asp Asp Lys Leu Tyr Arg Ala Asp Ser Arg Pro Pro Asp Glu Ile
1               5                   10                  15

Lys Gln Phe Arg Ser Leu Met Pro Arg Gly Ser Glu Tyr Phe Asp Arg
                20                  25                  30

Gly Thr Gln Met Asn Ile Asn Leu Tyr Asp His Ala Arg Gly Thr Gln
            35                  40                  45

Thr Gly Phe Val Arg His Asp Asp Gly Tyr Val Ser Thr Ser Ile Ser
50                  55                  60

Leu Arg Ser Ala His Leu Val Gly Gln Tyr Ile Leu Ser Gly His Ser
65                  70                  75                  80

Leu Thr Ile Tyr Ile Val Ile Ala Asn Met Phe Asn Val Asn Asp Val
                85                  90                  95

Ile Ser Ala Tyr Ser Pro His Pro Asp Glu Gln Glu Val Ser Ala Leu
            100                 105                 110

Gly Gly Ile Pro Tyr Ser Gln Ile Tyr Gly Trp Tyr Arg Val His Phe
        115                 120                 125

Gly Val Leu Asp Glu Gln Leu His Arg Asn Arg Gly Tyr Arg Asp Arg
130                 135                 140

Tyr Tyr Ser Asn Leu Asp Ile Ala Pro Ala Ala Asp Gly Tyr Gly Leu
145                 150                 155                 160

Ala Gly Phe Pro Pro Gln His Arg Ala Trp Arg Glu Glu Pro Trp Ile
                165                 170                 175

His His Ala Pro Pro Gly Cys Gly Asn Ala Pro Arg Ser Ser Met Ser
                180                 185                 190

Asn Thr Cys Asp Glu Lys Thr Gln Ser Leu Gly Val Lys Phe Leu Asp
                195                 200                 205

Glu Tyr Gln Ser Lys Val Lys Arg Gln Ile Phe Ser Gly Tyr Gln Ser
        210                 215                 220

Asp Ile Asp Thr His Asn Arg Ile Lys Asp Glu Leu
225                 230                 235